(12) United States Patent
Bruno et al.

(10) Patent No.: US 10,870,584 B2
(45) Date of Patent: Dec. 22, 2020

(54) INTEGRATED PROCESS AND PLANT FOR PRODUCTION OF UREA AND UAS (UREA-AMMONIUM SULPHATE) MIXTURES

(71) Applicant: SAIPEM S.p.A., San Donato Milanese (IT)

(72) Inventors: Lorenzo Bruno, San Donato Milanese (IT); Lino Carlessi, Dalmine (IT)

(73) Assignee: SAIPEM S.p.A., San Donato Milanese (IT)

( * ) Notice: Subject to any disclaimer, the term of this patent is extended or adjusted under 35 U.S.C. 154(b) by 0 days.

(21) Appl. No.: 16/461,279

(22) PCT Filed: Nov. 16, 2017

(86) PCT No.: PCT/IB2017/057167
§ 371 (c)(1),
(2) Date: May 15, 2019

(87) PCT Pub. No.: WO2018/092057
PCT Pub. Date: May 24, 2018

(65) Prior Publication Data
US 2019/0276325 A1    Sep. 12, 2019

(30) Foreign Application Priority Data

Nov. 16, 2016  (IT) .................. 102016000115907

(51) Int. Cl.
*C01C 1/242*  (2006.01)
*B01D 53/58*  (2006.01)
(Continued)

(52) U.S. Cl.
CPC .............. *C01C 1/242* (2013.01); *B01D 47/06* (2013.01); *B01D 53/58* (2013.01); *B01D 53/78* (2013.01);
(Continued)

(58) Field of Classification Search
None
See application file for complete search history.

(56) References Cited

U.S. PATENT DOCUMENTS 3,928,015 A * 12/1975 Siegel ................ C05C 3/00
71/28
2008/0092614 A1* 4/2008 Ingels .................. C01C 1/242
71/30

FOREIGN PATENT DOCUMENTS

GB         844294       8/1960
WO    WO2006/004424    1/2006
(Continued)

OTHER PUBLICATIONS

Notification Concerning Submission, Obtention or Transmittal of Priority Document for International Application No. PCT/IB2017/057167 dated Jan. 15, 2018.
(Continued)

*Primary Examiner* — Amy C Bonaparte
(74) *Attorney, Agent, or Firm* — Neal, Gerber & Eisenberg LLP

(57) ABSTRACT

An integrated process for production of urea and urea-ammonium sulphate ("UAS") comprises: a urea synthesis step carried out in a urea synthesis reactor; a recovery and concentration step, wherein a urea solution produced in the urea synthesis step is progressively concentrated in at least one recovery section and in a concentration section, recovering unreacted ammonia and carbon dioxide and water from said urea solution; a step of producing ammonium sulphate by reaction of sulphuric acid and ammonia in an ammonium sulphate production apparatus; a step of mixing said ammonium sulphate with concentrated urea coming from the concentration section to produce a UAS mixture; in the ammonium sulphate production step, at least a part of the
(Continued)

ammonia is provided by at least one off-gas containing ammonia and recovered from the recovery and concentration step.

13 Claims, 3 Drawing Sheets

(51) Int. Cl.
| | |
|---|---|
| *B01D 53/78* | (2006.01) |
| *B01J 4/00* | (2006.01) |
| *C07C 273/16* | (2006.01) |
| *C07C 273/04* | (2006.01) |
| *B01D 47/06* | (2006.01) |

(52) U.S. Cl.
CPC .............. *B01J 4/001* (2013.01); *C07C 273/04* (2013.01); *C07C 273/16* (2013.01); *B01D 2247/04* (2013.01); *B01D 2247/101* (2013.01); *B01J 2204/002* (2013.01); *B01J 2219/00006* (2013.01); *Y02P 20/10* (2015.11); *Y02P 20/141* (2015.11)

(56) References Cited

FOREIGN PATENT DOCUMENTS

| WO | WO2014/188371 | 11/2014 | |
| WO | WO-2016085343 A1 * | 6/2016 | ............ B01J 19/002 |

OTHER PUBLICATIONS

International Search Report and Written Opinion for International Application No. PCT/IB2017/057167 dated Feb. 13, 2018.

PCT Demand for International Preliminary Examination and Reply to International Search Report and the associated Written Opinion for International Application No. PCT/IB2017/057167 dated Sep. 12, 2018.

Notification of Receipt of Demand by Competent International Preliminary Examining Authority (Form PCT/IPEA/402) for International Application No. PCT/IB2017/057167 dated Sep. 18, 2018.

Notification of Transmittal of the International Preliminary Report on Patentability (Form PCT/IPEA/416) for International Application No. PCT/IB2017/057167 dated Oct. 30, 2018.

* cited by examiner

INTEGRATED PROCESS AND PLANT FOR PRODUCTION OF UREA AND UAS (UREA-AMMONIUM SULPHATE) MIXTURES

PRIORITY CLAIM

This application is a national stage application of PCT/IB2017/057167, filed on Nov. 16, 2017, which claims the benefit of and priority to Italian Patent Application No. 102016000115907, filed on Nov. 16, 2016, the entire contents of which are each incorporated by reference herein.

TECHNICAL FIELD

The present disclosure concerns an integrated process and plant for production of urea and urea-ammonium sulphate ("UAS") mixtures.

BACKGROUND

As known, urea is produced on an industrial scale by processes based on the reaction, in high temperature and high pressure conditions, between carbon dioxide and ammonia to form ammonium carbamate, and on the subsequent decomposition reaction of the ammonium carbamate to provide urea and water.

In general, the urea synthesis reaction is carried out in a reactor from which an aqueous solution of urea is obtained which is then progressively concentrated, with recovery and recycling of the non-converted reagents, and solidified in a finishing section (for example, a granulator or a prilling tower).

For example, in the traditional so-called "Snamprogetti" urea process, six sections are provided:
1. Synthesis and High Pressure (HP) Recovery Section;
2. Medium Pressure (MP) Purification and Recovery Section;
3. Low Pressure (LP) Purification and Recovery Section;
4. Vacuum Concentration Section;
5. Process Condensate Treatment Section;
6. Finishing Section by prilling or granulation.

In the synthesis and high pressure recovery section, NH3 and CO2 react in a reactor to give carbamate and urea (and water). As they exit the reactor, carbamate and urea are sent to a stripper where NH3, CO2 and ammonium carbamate are recovered and recycled to the reactor.

The bottom outlet of the stripper is connected to the medium pressure (MP) purification and recovery section, where the carbamate, not decomposed in the stripper, is decomposed at approximately 18 bar in a first decomposer/exchanger (for example, using steam). The decomposition products are NH3 and CO2, which are also recycled to the urea reactor, together with the products recovered by the low pressure purification and recovery section.

The bottom of the medium pressure purification and recovery section is connected to the low pressure purification and recovery section, where the remaining carbamate is decomposed at approximately 4.5 bar in another decomposer/exchanger (for example, again using steam). NH3, CO2 and water flow out of the head of the medium pressure decomposer, and after condensation are recycled to the reactor together with NH3, CO2 and water coming from the low pressure section.

The urea coming out of the low pressure section is concentrated in the vacuum concentration section to values of approximately 96% to 99.7% before being sent to the granulator or the prilling tower to obtain the end product in the form of granulated or prilled urea.

Of the various uses of urea, use as nitrogen fertilizer is particularly important, due to the relatively very high nitrogen content. On the other hand, some intensive crops, for example wheat, rice, cotton, tea, etc., require not only nitrogen but also potassium, phosphorous and sulphur for a relatively higher production yield.

Nitrogen and potassium are the elements most required, but phosphorous and sulphur are also relatively important for relatively good production yield.

In particular, sulphur combined with urea performs two fundamental functions: it increases productivity in crops where it is used; and makes the nitrogen of the urea more available in the ground, limiting dispersion thereof in the atmosphere.

The use of a liquid mixture of urea and ammonium sulphate known as UAS as a fertilizer has therefore become widespread; in the UAS, the presence of sulphur (indicatively around 5%) ensures performance of the above-mentioned functions. This liquid mixture is generally solidified and granulated in order to be relatively better applied to the various types of crops.

The UAS mixture for use as fertilizer can be prepared for example with urea from a traditional urea plant and granulated together with ammonium sulphate produced from ammonia and sulphuric acid in an appropriate reactor, typically in a pipe reactor.

At the moment, the urea and UAS production lines are substantially autonomous or have a relatively very low level of integration; in particular, the ammonium sulphate production plant has a relatively very low level of integration in the urea production process.

A relatively greater and improved integration of the urea process/plant with the UAS production process/plant would be desirable, leading to an increase in the production efficiency of urea, ammonium sulphate and/or UAS.

SUMMARY

One object of the present disclosure is to provide an integrated process and plant for the production of urea and urea-ammonium sulphate ("UAS") mixtures which overcome certain of the above-mentioned drawbacks of certain of the known art; in particular, one object of the disclosure is to improve the efficiency of the joint production of urea and UAS mixtures.

In certain embodiments, the present disclosure concerns an integrated urea and urea-ammonium sulphate production process including a urea synthesis step carried out in a urea synthesis reactor, a recovery and concentration step in which a urea solution produced in the urea synthesis step is progressively concentrated in at least one recovery section including at least a medium pressure recovery section and a low pressure recovery section, and in a concentration section located downstream of the at least one recovery section to recover unreacted ammonia and carbon dioxide and water from the urea solution, an ammonium sulphate production step that occurs by reaction of sulphuric acid and ammonia in an ammonium sulphate production apparatus, wherein at least a part of the ammonia is from at least one off-gas containing ammonia and recovered from the recovery and concentration step, a mixing step of the ammonium sulphate with concentrated urea from the concentration section to produce a urea-ammonium sulphate mixture, and a urea finishing step in which the mixture of ammonium sulphate and urea is one of granulated and prilled.

In certain embodiments, the present disclosure concerns an integrated urea and urea-ammonium sulphate production plant including a urea synthesis reactor, at least one recovery section including at least a medium pressure recovery section and a low pressure recovery section, a concentration section arranged downstream of the at least one recovery section, a finishing section, a main urea line connecting a product outlet of the urea synthesis reactor with the at least one recovery section, the concentration section and the finishing section, an ammonium sulphate production apparatus with a sulphuric acid supply circuit, and at least one off-gas line connecting at least one gas outlet of the at least one recovery section with the ammonium sulphate production apparatus to supply the ammonium sulphate production apparatus with at least one off-gas containing ammonia recovered from the at least one recovery section such that in the ammonium sulphate production apparatus, ammonium sulphate is produced by reaction of the ammonia contained in the at least one off-gas with the sulphuric acid supplied via the sulphuric acid supply circuit.

The disclosure provides an integrated process and plant for the joint production of urea and UAS mixtures which enable urea and UAS to be produced with increased efficiency compared to certain of the known art. That is, according to the disclosure, off-gases of the urea plant containing ammonia are used in the production of UAS (in particular, to produce ammonium sulphate), thus recovering the ammonia.

Furthermore, according to the disclosure, water drawn from the urea production cycle is used in the production of UAS; since the water is unfavourable to the urea formation reaction, reduction of the water content in the urea process and its use in the UAS production process increases the conversion in the urea synthesis reactor.

In the plant/process of the disclosure, an apparatus for the production of ammonium sulphate is effectively integrated in a urea plant. According to the disclosure, the ammonium sulphate production apparatus is not a traditional pipe reactor or other reactor normally used for the production of ammonium sulphate, but an apparatus purposely conceived to be integrated in the urea process/plant, namely a multi-stage cyclonic spray scrubber.

The off-gases containing ammonia coming from the urea plant, namely from the low pressure decomposer and from the low and medium pressure condensers, are sent to said cyclonic scrubber. The ammonia contained in these off-gases is made to react with nebulized sulphuric acid. The exothermic reaction enables ammonium sulphate in powder to be obtained; the powder is separated from the gases by the cyclonic scrubber and mixed with liquid urea on the bottom of said cyclonic scrubber to form the urea-ammonium sulphate (UAS) mixture.

The reaction between sulphuric acid and ammonia, being exothermic, can lead to an excessive increase in the temperature of the gases and powders in the cyclonic scrubber. To control the temperature (maintaining it in particular around 150° C. to 200° C.), an aqueous solution can be used coming from the condenser of the low pressure section, or from condensation of the water coming from the gases exiting the cyclonic scrubber.

Furthermore, part of the heat of the reaction between ammonia and sulphuric acid can be used to make water evaporate from the urea coming from the low pressure section and sent to the bottom of the cyclonic scrubber.

The ammonium sulphate produced in the cyclonic scrubber is mixed with urea to form a eutectic in which the concentration of the ammonium sulphate is lower than 70%: this enables the mixture coming out of the cyclonic scrubber to be maintained molten with temperatures lower than 150° C.

The mixture is then sent to the finishing section for solidification (granulation or prilling) together with the remaining urea to form a UAS mixture in the desired concentrations.

The gases coming out of the cyclonic scrubber and containing hydrogen, oxygen, nitrogen, methane and CO2 with a temperature above 150° C. can be sent to a catalytic combustor, where the hydrogen and the methane are transformed into water and CO2. The gases coming out of the catalytic combustor can be cooled to temperatures down to 70° C. to recover heat and to heat air which can be used, for example, in the finishing section granulator. From the cold gases, condensation water can be recovered which can be partially sent to the cyclonic scrubber for control of the temperature; the remainder of the recovered water is sent to the process condensates treatment section.

Alternatively, especially when there is a prilling tower for solidification of the urea, the gases coming out of the catalytic combustor can be cooled with a boiler to recover heat and produce steam for use in the urea plant. The gases coming out of the boiler can be sent to an exchanger to be cooled down to 70° C. Also in this case, condensation water is recovered from the cold gases, which can be partly sent to the cyclone for control of the temperature, and partly sent to the process condensates treatment section.

The main advantages achieved by the disclosure are therefore the following:
1. complete elimination of the emissions of ammonia from the off-gases discharged into the atmosphere;
2. reduction of recycling of water to the urea synthesis reactor with consequent increase in conversion yield;
3. reduction of the cooling water used for cooling and condensation of the gases coming from the low pressure section decomposer head;
4. recovery of the ammonia and sulphuric acid reaction heat;
5. recovery of the combustion heat of the off-gases without the formation of nitrogen oxides.

Additional features are described in, and will be apparent from the following Detailed Description and the figures.

BRIEF DESCRIPTION OF THE DRAWINGS

Further characteristics and advantages of the present disclosure will appear clear from the description of the following non-limiting embodiment examples, with reference to the figures of the attached drawings, in which.

DETAILED DESCRIPTION

Figure 1:
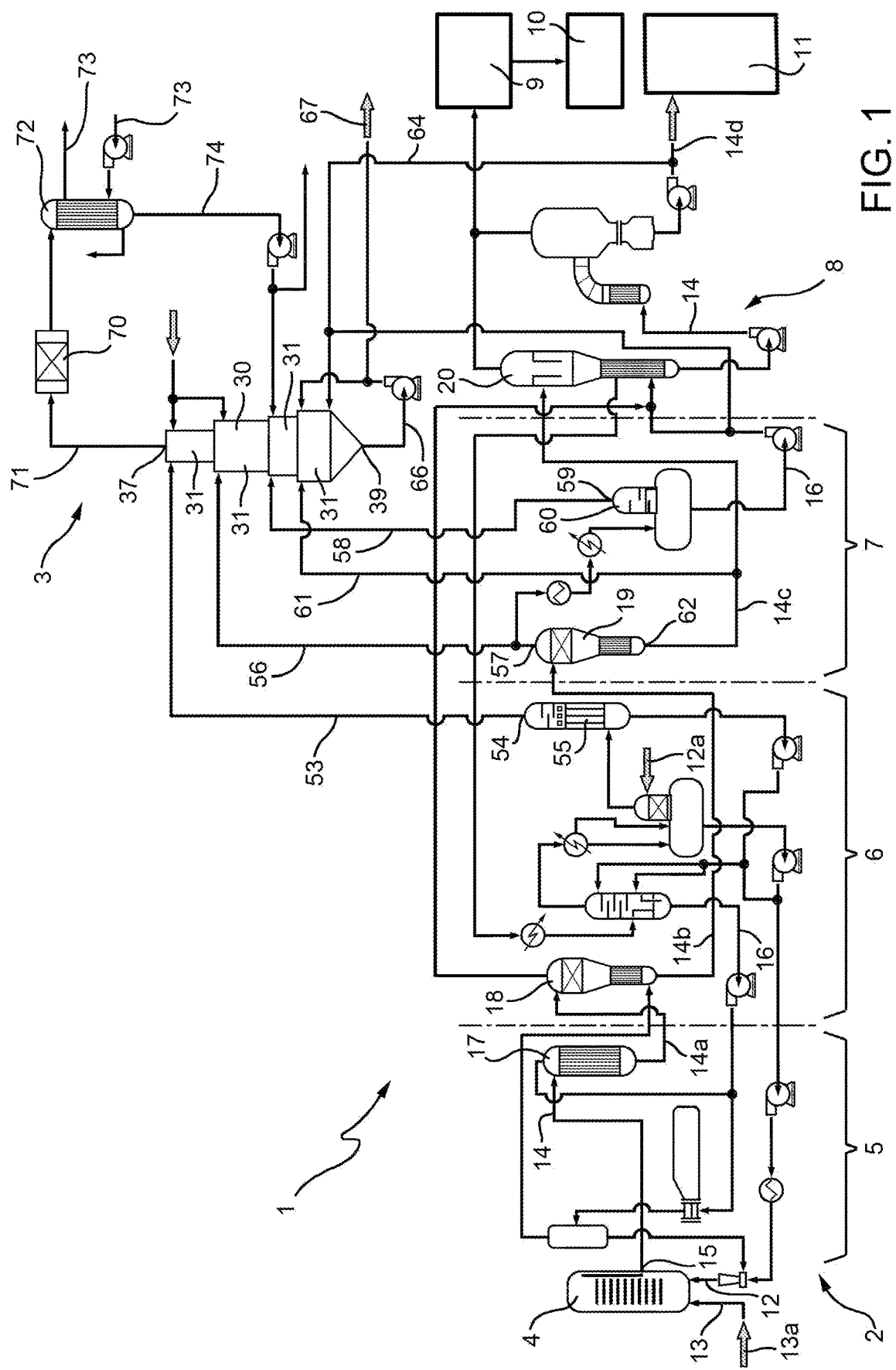
FIG. 1 is a schematic view of an integrated plant for production of urea and urea-ammonium sulphate ("UAS") mixtures according to the disclosure.

In FIG. 1 the number 1 indicates as a whole an integrated plant for the production of urea and urea-ammonium sulphate ("UAS") mixture, implementing the integrated process for the production of urea and UAS according to the disclosure.

The plant 1 comprises a urea plant 2 and an apparatus 3 for the production of ammonium sulphate.

The urea plant 2, and likewise the urea production process carried out therein, can be of various types.

Here reference is made, purely by way of example, to a plant/process for the production of urea according to the known "Snamprogetti" technology. It is understood that the disclosure also applies to other plants/processes for the production of urea.

In the non-limiting configuration illustrated, but not necessarily, the urea plant 2 comprises: a reactor 4 for the synthesis of urea where a reaction takes place for the synthesis of urea from ammonia and carbon dioxide; recovery sections 5, 6, 7, in particular a high pressure recovery section 5, a medium pressure recovery section 6 and a low pressure recovery section 7, in which a solution of urea produced in the reactor 4 is progressively concentrated with removal from it of unreacted ammonia and carbon dioxide and water, and recirculation of the recovered components; a vacuum concentration section 8 provided with a vacuum system 9 and connected to a section 10 for treatment of the process condensates (essentially, water); a finishing/solidification section 11, comprising for example a granulator or a prilling tower.

The components of the various sections are not all described in detail below, only the main ones useful for understanding the present disclosure.

The reactor 4 is supplied with NH3 and CO2 via respective supply lines 12, 13, connected to respective inlets 12a, 13a through which NH3 and CO2 enter the plant 1. A main urea line 14 connects a product outlet 15 of the reactor 4 to the recovery sections 5, 6, 7 and to the vacuum concentration section 8. A recovery circuit 16 (comprising various apparatus and lines, not described in detail for the sake of simplicity) connects the recovery sections 5, 6, 7 and the concentration section 8 to one another and to the NH3 supply line 12 to recirculate to the reactor 4 unreacted components recovered by the recovery sections 5, 6, 7.

In particular, the main urea line 14 connects in series (by respective line sections): the reactor 4; a stripper 17 of the high pressure recovery section 5; a medium pressure decomposer 18 in the medium pressure recovery section 6; a low pressure decomposer 19 in the low pressure recovery section 7; an exchanger/concentrator 20 in the concentration section 8; a granulator or a prilling tower (not illustrated in detail) of the finishing/solidification section 11.

In the stripper 17, arranged along the main urea line 14, non-converted NH3 and CO2 and ammonium carbamate are recovered and recycled to the reactor 4 via the recovery circuit 16.

The stripper 17 has a bottom outlet connected, by a portion 14a of the main urea line 14, to the medium pressure recovery section 6 and in particular to the medium pressure decomposer 18, where the carbamate is decomposed (for example at approximately 18 bar using steam) to give NH3 and CO2, which are extracted from a head outlet of the decomposer 18 and recycled to the reactor 4 by the recovery circuit 16.

The medium pressure decomposer 18 is in turn connected by a further portion 14b of the main urea line 14 to the low pressure decomposer 19, where the remaining carbamate is decomposed (for example, at approximately 4.5 bar using steam).

A further portion 14c of the main urea line 14 connects a bottom outlet of the low pressure decomposer 19 to the concentration section 8, in particular to the exchanger/concentrator 20 where the urea solution flowing out of the low pressure recovery section 7 is concentrated to values of approximately 96÷99.7% before being sent, through a section 14d of the main urea line 14, to the finishing/solidification section 11 to be granulated or prilled.

In the recovery sections 5, 6, 7 off-gases containing ammonia are produced, in particular along the recovery circuit 16; furthermore, off-gases rich in ammonia and water flow out of the low pressure decomposer 19.

According to the disclosure, these off-gases are used in the apparatus 3 for production of ammonium sulphate to produce ammonium sulphate and subsequently UAS.

In certain embodiments, as shown in FIG. 1, off-gases containing ammonia produced in the medium pressure recovery section 6 and in the low pressure recovery section 7 are sent to the apparatus 3. However, off-gases coming from the high pressure recovery section 5 can also be used, together with or alternatively to the preceding ones.

The apparatus 3 comprises a multistage cyclonic scrubber 30, where the ammonia contained in the off-gases recovered from the urea plant 2 reacts with sulphuric acid to form ammonium sulphate.

Figure 2:
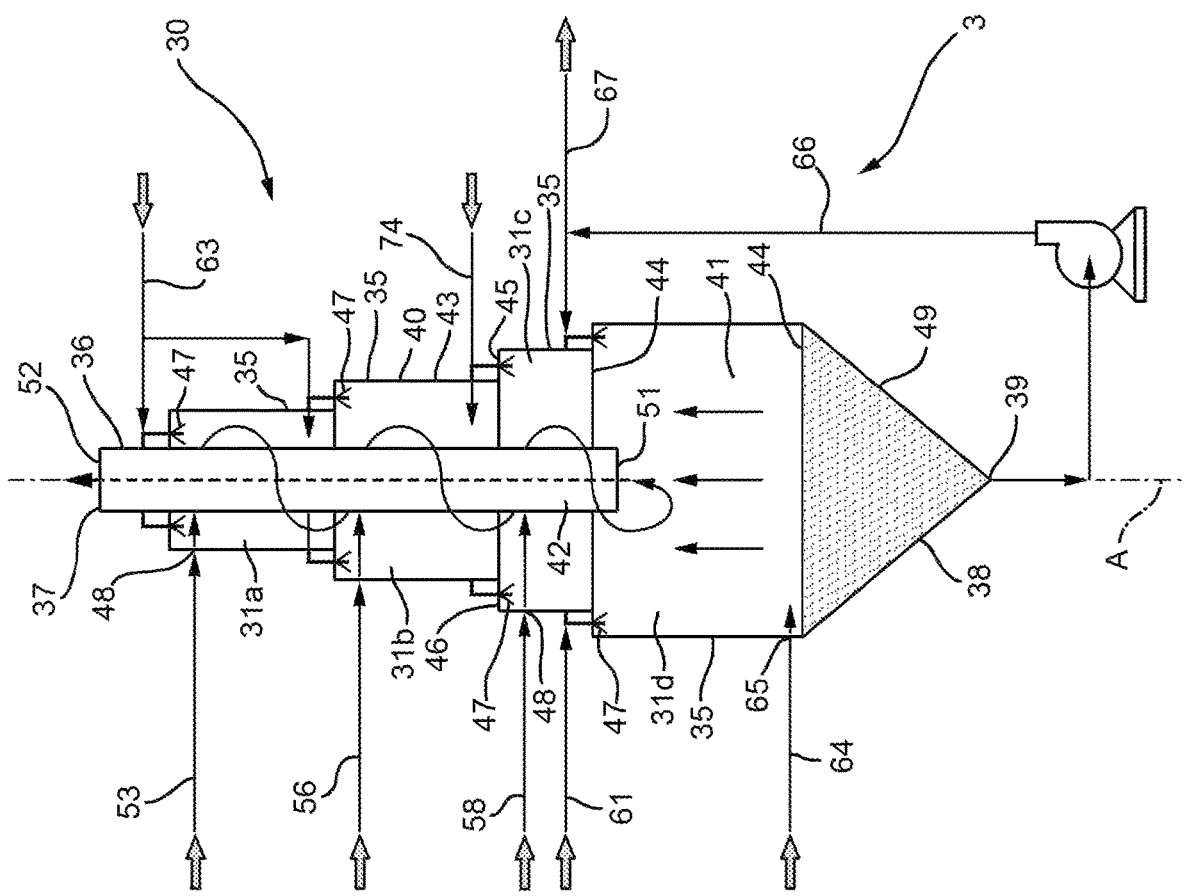
FIG. 2 is a schematic view in longitudinal section of an apparatus forming part of the plant of FIG. 1.

With reference also to FIG. 2, the cyclonic scrubber 30 comprises a plurality of stages 31, defined by respective cyclones 35 in series.

In the non-limiting example illustrated, but not necessarily, the cyclonic scrubber 30 comprises four stages 31a, 31b, 31c, 31d.

In particular, the cyclonic scrubber 30 extends substantially along a longitudinal axis A, vertical in use, between an upper end 36, provided with a head outlet 37, and a lower end 38, provided with a bottom outlet 39; the cyclonic scrubber 30 has an outer casing 40 delimiting an internal treatment chamber 41.

The stages 31 are arranged in series along the axis A, from the upper end 36 (where the first stage 31a is located) to the lower end 38 (where the fourth stage 31d is located).

The chamber 41 houses a central tubular body 42, positioned along the axis A and communicating with the head outlet 37.

The cyclones 35 defining the respective stages 31 are arranged one above the other along the axis A and communicate internally with one another.

In certain embodiments, the cyclones 35 define respective portions of the chamber 41 and are delimited by respective portions of lateral wall 43, for example substantially cylindrical, of the casing 40.

The cyclones 35 have, in certain embodiments, dimensions, in particular diameter, increasing downwards along the axis A (i.e., towards the lower end 38 provided with bottom outlet 39).

Each cyclone 35 (i.e., each stage 31) extends along and around the axis A between an open lower end 44 and an upper head 45 provided with an annular flange 46, equipped with an injection device 47.

In certain embodiments, each injection device 47 has a plurality of nozzles distributed on the respective flange 46 and angularly spaced from one another along the flange 46.

Each cyclone 35 has a tangential inlet 48, obtained in the respective portion of lateral wall 43 in the vicinity of the flange 46 and below the flange 46.

Below the last stage 31d, a collection portion 49 is arranged tapered towards the lower end 38 and the bottom outlet 39.

The tubular body 42 has a lower opening 51, positioned at the top of the stage 31d (stage 31 lower (i.e., closer to the lower end 38)), and an upper opening 52 defining or communicating with the head outlet 37.

In certain embodiments, the cyclonic scrubber 30 is made of carbon steel coated internally with a fluoropolymer resin (like PFA) resistant to temperatures up to 300° C. and to acid environments.

The plant 1 comprises:
- a medium pressure off-gas line 53, which connects a gas outlet 54 of the medium pressure recovery section 6, in particular a head gas outlet of an absorber 55 of the medium pressure recovery section 6, to the apparatus 3, namely to the inlet 48 of the first stage 31a of the cyclonic scrubber 30 (the absorber 55 having a bottom outlet from which a condensate recovered in the absorber 55 recirculates);
- a first low pressure off-gas line 56, which connects a first gas outlet 57 of the low pressure recovery section 7, in particular a head gas outlet of the low pressure decomposer 19, to the apparatus 3, namely to the inlet 48 of the second stage 31b;
- a second low pressure off-gas line 58, which connects a second gas outlet 59 of the low pressure recovery section 7, in particular a head gas outlet 59 of an absorption tower 60 of the low pressure recovery section 7, to the apparatus 3 and namely to the inlet 48 of the third stage 31c (the absorption tower 60 having a bottom outlet connected to the concentration section 8); and
- a urea line 61 that connects a urea outlet 62 of the low pressure recovery section 7, in particular a bottom urea outlet 62 of the low pressure decomposer 19, to the apparatus 3, namely to the injection device 47 of the fourth stage 31d.

If the off-gas of the high pressure section 5 is (also) recovered, the plant 1 can comprise a high pressure off-gas line (not illustrated), which connects for example a gas outlet of the high pressure recovery section 5, in particular a head gas outlet of the stripper 17, to the apparatus 3, namely to the first stage 31a of the cyclonic scrubber 30 (in said case, the high pressure off-gas line can join, for example, the medium pressure off-gas line 53, or enter the apparatus 3 from a dedicated inlet).

In the first stage 31a (positioned at the upper end 36 of the cyclonic scrubber 30), the off-gases coming from the medium pressure recovery section 6 are supplied by the off-gas line 53, and sulphuric acid is supplied by a sulphuric acid supply circuit 63 connected to the injection device 47, which nebulizes the sulphuric acid into the off-gases supplied to stage 31a. The sulphuric acid reacts with the ammonia present in the off-gases, producing ammonium sulphate and ammonium bisulphate.

The gases coming from the first stage 31a pass to the second stage 31b through the open lower end 44 of the first stage 31a.

The cyclone 35 of the second stage 31b is positioned below the cyclone 35 of the first stage 31a along the axis A and has a larger diameter than the latter.

In the second stage 31b the off-gases coming from the head gas outlet 57 of the low pressure decomposer 19 are fed through the inlet 48.

In the second stage 31b, the main part of the reaction of the ammonia with sulphuric acid and ammonium bisulphate takes place; to complete the reaction, from the head 45 of this stage 31b, further sulphuric acid is nebulized by the respective injection device 47 connected to the sulphuric acid supply circuit 63.

The gases coming from the second stage 31b pass to the third stage 31c, positioned below the second stage 31b and having a cyclone 35 with an even larger diameter. In the third stage 31c the off-gases coming from the absorption tower 60 of the low pressure recovery section 7 are introduced through the inlet 48.

In the third stage 31c the reaction of the ammonium bisulphate with the ammonia present in gaseous phase is completed.

The reaction between ammonia and sulphuric acid, since it is highly exothermic, can lead to a considerable increase in the temperature of the gases in the first three stages 31 of the cyclonic scrubber 30: said temperature increase could entail problems in the fourth stage 31d, in the case of high temperatures in contact with the urea.

It is therefore expedient to control the temperature of the third stage 31c maintaining it at approximately 150° C. to 200° C.; the temperature of the third stage 31c can be controlled, for example by injecting water coming from a solution of water and ammonia drawn from the low pressure recovery section 7, or from condensation of the water contained in the gases exiting the cyclonic scrubber 30 (as described in detail below).

The gases coming from the third stage 31c pass to the fourth stage 31d, positioned below the third stage 31c and having a cyclone 35 with a diameter greater than the cyclones 35 of all the preceding stages 31.

In the fourth stage 31d the ammonium sulphate coming from the preceding stages 31 is mixed with urea to form a mixture of urea and ammonium sulphate (UAS).

For example, in the fourth stage 31d an aqueous solution of urea (containing around 70% of urea) coming from the low pressure decomposer 19 can be sent through the urea line 61; this enables heat to be recovered in order to evaporate the water contained in said solution. The urea is advantageously nebulized from the head 45 of the fourth stage 31d (being supplied to the stage 31d by the respective injection device 47) to facilitate contact with the gases and the ammonium sulphate.

At the lower end 44 of the fourth stage 31d urea is supplied coming from the concentration section 8 in order to correct the concentration of the ammonium sulphate (below 70%). The urea is supplied to the fourth stage 31d through a urea line 64 which connects the section 14d of the main urea line 14 in the concentration section 8 to an auxiliary inlet 65 of the fourth stage 31d, positioned at the lower end 44.

In particular, in the fourth stage 31d urea is introduced in a quantity such as to form a eutectic of urea and ammonium sulphate; the eutectic of urea and ammonium sulphate is low-melting and manageable at temperatures of 150° C.

The eutectic of urea and ammonium sulphate produced in the fourth stage 31d flows out of the cyclonic scrubber 30 through the bottom outlet 39 and can be partly recycled, through a recirculation line 66, to the head 45 of the fourth stage 31d, by the respective injection device 47 (adding to the urea coming from the urea line 61), to complete any evaporation of the water; the remainder is sent to the finishing/solidification section 11 by an outlet line 67.

The gases purified from the ammonia and containing water, $CO_2$, methane, hydrogen, nitrogen and oxygen flow out of the head outlet 37 of the cyclonic scrubber 30.

Said gases, having a temperature roughly higher than 150° C. and containing hydrogen, methane and oxygen, can be sent to a catalytic combustor 70 connected to the head outlet 37 by a gas line 71, to be burnt, thus developing heat. The gases flowing out of the combustor 70 at maximum temperature of 500° C. can be sent to an exchanger 72 to pre-heat air, circulating through the exchanger 72 and to an air circuit 73 connected to the finishing/solidification section 11, where the air is used, for example, in a granulator.

In the exchanger 72 the temperature can be brought to around 70° C. causing condensation of part of the water contained in the gases.

The water condensed in the exchanger 72 can be recovered and partially used for control of the temperature in the cyclonic scrubber 30, since it is supplied by a water recovery line 74 which connects a bottom outlet of the exchanger 72 to the injection device 47 of the third stage 31c.

Figure 3:
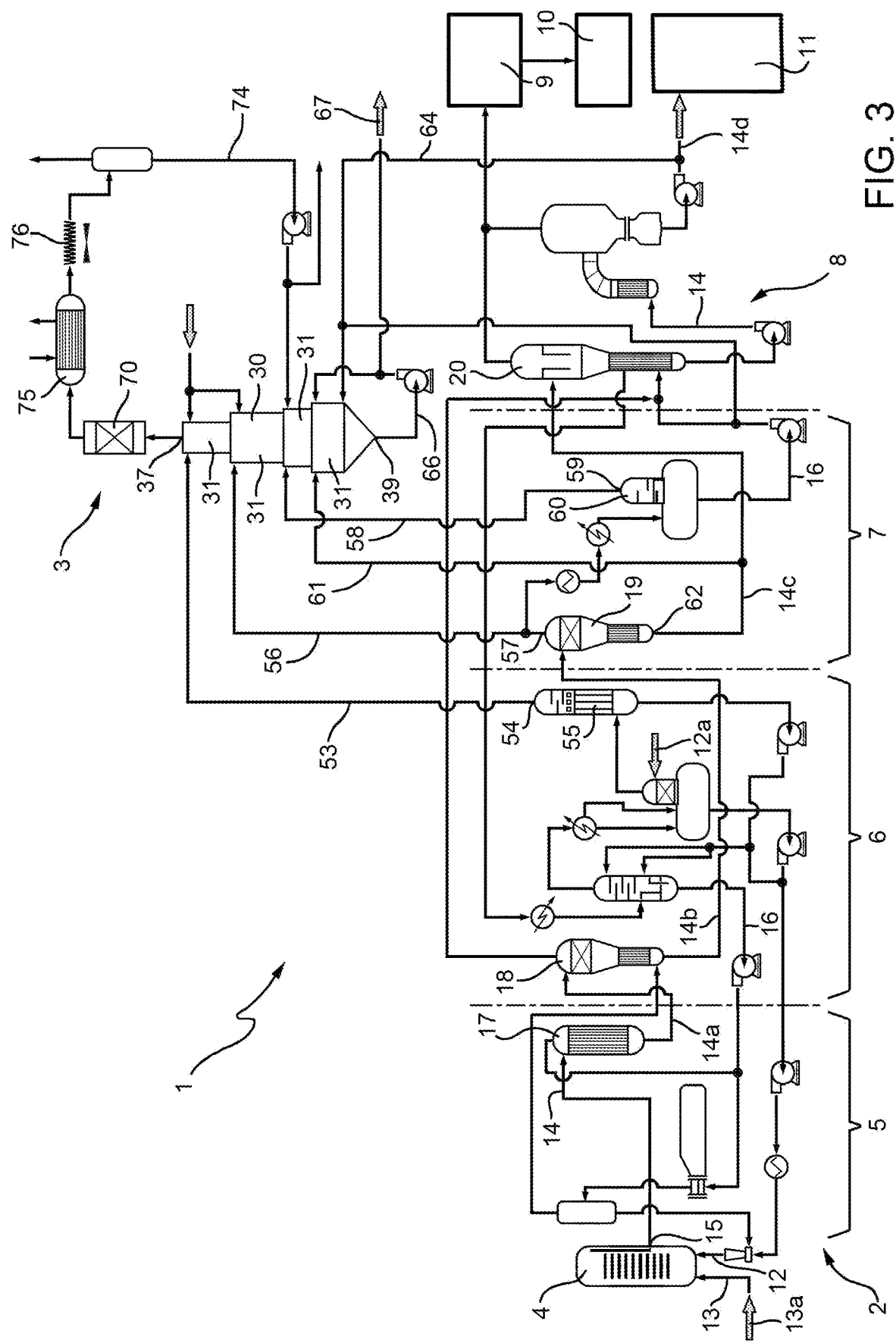
FIG. 3 is a schematic view of a variation of the integrated plant of FIG. 1.

Alternatively, above all when the finishing/solidification section 11 comprises a prilling tower, the gases flowing out of the combustor 70 at maximum temperature of 500° C. can be sent, as shown in FIG. 3, to a boiler 75 to produce steam at low pressure (for example 4.5 bar) which can be used in the urea plant 2.

At the outlet of the boiler 75 it is possible to insert a heat exchanger 76 (air cooler) to bring the temperature to around 70° C., causing part of the water contained in the gases to condense.

Also in this case, the water can be recovered and partially used for control of the temperature in the cyclonic scrubber 30, since it is supplied to the injection device 47 of the third stage 31c by the water recovery line 74.

Lastly, it is understood that further modifications and variations that do not depart from the scope of the attached claims can be made to the integrated process and plant for production of urea and urea-ammonium sulphate ("UAS") mixtures described and illustrated here. As such, it should be appreciated that variants can be made regarding the present disclosure with respect to the embodiments described with reference to the accompanying figures without departing from the scope of the claims. Accordingly, various changes and modifications to the presently disclosed embodiments will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. An integrated urea and urea-ammonium sulphate production process comprising:
   a urea synthesis step carried out in a urea synthesis reactor;
   a recovery and concentration step in which a urea solution produced in the urea synthesis step is progressively concentrated in at least one recovery section comprising at least a medium pressure recovery section and a low pressure recovery section, and in a concentration section located downstream of said at least one recovery section to recover unreacted ammonia and carbon dioxide and water from said urea solution;
   an ammonium sulphate production step carried out in a plurality of stages in series and that occurs by reaction of sulphuric acid and ammonia in an ammonium sulphate production apparatus, wherein:
      at least a part of the ammonia is from at least one off-gas containing unreacted ammonia from the urea solution produced in the urea synthesis step that is recovered from the recovery and concentration step,
      the at least one off-gas is a medium pressure off-gas from a head outlet of a condenser of the medium pressure recovery section and is supplied to a first stage of the ammonium sulphate production step,
      a first low pressure off-gas is supplied from a gas head outlet of a low pressure decomposer of the low pressure recovery section and is supplied to a second stage of the ammonium sulphate production step, and
      a second low pressure off-gas is supplied from a head outlet of an absorption tower of the low pressure recovery section and is supplied to a third stage of the ammonium sulphate production step;
   a mixing step of mixing said ammonium sulphate with concentrated urea from the concentration section to produce a urea-ammonium sulphate mixture; and
   a urea finishing step in which the mixture of ammonium sulphate and urea is granulated or prilled.

2. The integrated urea and urea-ammonium sulphate production process of claim 1, further comprising a supplying step of supplying the ammonium sulphate production apparatus with a solution of urea produced in the low pressure recovery section of the recovery and concentration step.

3. The integrated urea and urea-ammonium sulphate production process of claim 1, wherein a urea solution is supplied from a bottom urea outlet of the low pressure decomposer of the low pressure recovery section and is supplied to a fourth stage of the ammonium sulphate production step.

4. The integrated urea and urea-ammonium sulphate production process of claim 1, further comprising:
   drawing gases, purified from the ammonia and containing methane, hydrogen and oxygen, from the ammonium sulphate production step;
   burning said drawn gases; and
   transferring heat generated by the burning of said gases to an air stream, wherein the transferred heat is at least one of: used for the urea finishing step and further transferred to a water stream to produce steam.

5. The integrated urea and urea-ammonium sulphate production process of claim 4, further comprising:
   a condensing step of condensing water from any gases combusted in the burning of said drawn gases; and
   supplying the condensed water to the ammonium sulphate production step to control a temperature in said ammonium sulphate production step.

6. An integrated urea and urea-ammonium sulphate production process comprising:
   a urea synthesis step carried out in a urea synthesis reactor;
   a recovery and concentration step in which a urea solution produced in the urea synthesis step is progressively concentrated in at least one recovery section comprising at least a medium pressure recovery section and a low pressure recovery section, and in a concentration section located downstream of said at least one recovery section to recover unreacted ammonia and carbon dioxide and water from said urea solution;
   an ammonium sulphate production step that occurs by reaction of sulphuric acid and ammonia in an ammonium sulphate production apparatus, wherein at least a part of the ammonia is from at least one off-gas containing unreacted ammonia from the urea solution produced in the urea synthesis step that is recovered from the recovery and concentration step;
   drawing gases, purified from the ammonia and containing methane, hydrogen and oxygen, from the ammonium sulphate production step;
   burning said drawn gases;
   transferring heat generated by the burning of said gases to an air stream, wherein the transferred heat is at least one of: used for a urea finishing step and further transferred to a water stream to produce steam;

a mixing step of mixing said ammonium sulphate with concentrated urea from the concentration section to produce a urea-ammonium sulphate mixture; and the urea finishing step in which the mixture of ammonium sulphate and urea is granulated or prilled.

7. The integrated urea and urea-ammonium sulphate production process of claim 6, further comprising a feeding step of feeding said ammonium sulphate production apparatus with the at least one off-gas recovered from at least one of the recovery sections.

8. The integrated urea and urea-ammonium sulphate production process of claim 6, wherein the at least one off-gas is at least one of a medium pressure off-gas from the medium pressure recovery section and at least one low pressure off-gas from the low pressure recovery section.

9. The integrated urea and urea-ammonium sulphate production process of claim 6, further comprising a supplying step of supplying the ammonium sulphate production apparatus with a solution of urea produced in the low pressure recovery section of the recovery and concentration step.

10. The integrated urea and urea-ammonium sulphate production process of claim 6, wherein the ammonium sulphate production step is carried out in a plurality of stages in series.

11. The integrated urea and urea-ammonium sulphate production process of claim 10, wherein said at least one off-gas is a medium pressure off-gas from a head outlet of a condenser of the medium pressure recovery section and is supplied to a first stage of the ammonium sulphate production step.

12. The integrated urea and urea-ammonium sulphate production process of claim 11, wherein a first low pressure off-gas is supplied from a gas head outlet of a low pressure decomposer of the low pressure recovery section and is supplied to a second stage of the ammonium sulphate production step.

13. The integrated urea and urea-ammonium sulphate production process of claim 6, further comprising:

a condensing step of condensing water from any gases combusted in the burning of said drawn gases; and supplying the condensed water to the ammonium sulphate production step to control a temperature in said ammonium sulphate production step.

* * * * *